United States Patent [19]

Goldberg

[11] Patent Number: 5,303,819
[45] Date of Patent: Apr. 19, 1994

[54] DISPLAY HOLDER FOR TEETH

[76] Inventor: Eileen S. Goldberg, 4944 Palo Dr., Tarzana, Calif. 91356

[21] Appl. No.: 18,639

[22] Filed: Feb. 17, 1993

[51] Int. Cl.⁵ .................. A61C 19/10; A61B 19/02
[52] U.S. Cl. .................................. 206/83; 206/63.5
[58] Field of Search ............................ 206/83, 63.5

[56] References Cited

U.S. PATENT DOCUMENTS

| | | |
|---|---|---|
| 1,702,312 | 2/1929 | Pickering . |
| 2,196,566 | 4/1940 | Sabattis . |
| 2,444,294 | 6/1948 | Jones . |
| 2,620,919 | 12/1952 | Passmore . |
| 3,051,308 | 8/1962 | Estrem . |
| 4,694,956 | 9/1987 | Sims . |
| 4,775,318 | 10/1988 | Breslin .................. 206/63.5 X |
| 4,923,058 | 5/1990 | Dennison .................. 206/83 |
| 5,050,729 | 9/1991 | Karbowniczak .......... 206/83 |
| 5,203,450 | 4/1993 | Benetti .................... 206/63.5 |

*Primary Examiner*—William I. Price
*Attorney, Agent, or Firm*—Townsend and Townsend Khourie and Crew

[57] ABSTRACT

A tooth holder is provided with U-shaped storage members that have multiple transparent compartments each accommodating a particular tooth. Each storage member includes a base in which a set of the compartments are formed and a detachable cover therefor. The cover snaps on top of a respective base to hold the teeth in the compartments in place. The storage members are secured to a casing having a hinge such that the storage members can be pivoted and secured one on top of the other for storage. The casing includes a shelf that extends beyond each base so that a label indicating the date of tooth loss can be placed on the shelf adjacent the compartment in which the tooth is placed.

14 Claims, 2 Drawing Sheets

DISPLAY HOLDER FOR TEETH

BACKGROUND OF THE INVENTION

The invention relates to display receptacles generally, and more particularly to a receptacle for holding and displaying teeth detached from the natural support structure in a person's mouth.

U.S. Pat. No. 4,694,956 discloses a display receptacle for the deciduous teeth of a child when successive ones of the child's primary teeth are lost. The receptacle includes a number of storage compartments which are preferably formed of transparent material in order that the teeth may be observed after placement therein. The separate compartments are arranged along either an upper or lower U-shaped member. Each compartment includes a hinge so that it can be pivoted away from the U-shaped member when it is desired to place a tooth in the display receptacle. The compartment is then pivoted back toward the U-shaped member to its closed position. A disadvantage of this construction is that the plurality of individual compartments, each including its own hinge and being secured to a housing member, results in a relatively complex structure for manufacture. In addition, the receptacle does not include a mechanism to reflect the date of loss of each of the teeth stored therein, which is important for prospective interceptive orthodontia.

SUMMARY OF THE INVENTION

The present invention is directed to a display holder for teeth that avoids the problems and disadvantages of the prior art. The tooth holder includes a casing and top and bottom U-shaped storage members which are secured to the casing to simulate upper and lower gum supporting regions of a persons mouth. Each storage member includes a U-shaped base member and a cover member. A plurality of receptacles, formed in each base member, are configured for receiving the variously sized teeth. Each cover member is constructed as a one-piece shell having a recess configured to receive one of the base members and, thus, secure teeth placed in respective receptacles and prevent them from falling out of the base member. The onepiece corner construction also enables one to simultaneously cover (for storage) or uncover (for viewing) all of the receptacles in a base member. That is, the detachable covers snap onto the top of each of the storage members to hold the teeth in place. Since each storage member is formed by a single base member and cover, manufacture and use of the device is relatively simple. The casing comprises two end portions pivotally coupled to one another by a narrowed portion which acts as a hinge. The top storage member is secured to one end portion and the bottom storage member is secured to the other end portion so that the storage members can be pivoted toward or away from one another depending on whether access to the receptacles is desired. The casing preferably comprises a single sheet of flexible material so that it can be readily cut from a blank, for example. Since each storage member is identical and each cover is identical, only three pieces need be inventoried for manufacture.

Another advantageous feature of the tooth holder is the provision of a shelf adjacent the receptacles for recording tooth loss. Specifically, each end portion of the casing includes a portion forming a shelf that extends radially outward from a respective storage member and is configured to receive a label indicating the date of loss of a tooth placed in the receptacle adjacent the label. In use, a child's detached tooth is placed in a receptacle of the storage member and a label indicating the date of loss of the tooth is placed adjacent the receptacle. Alternatively, the shelf can comprise a material suitable for print, such as paper or cardboard, so that the date of loss can be marked directly on the tooth holder shelf without the need for discrete labels. In this way, a record of tooth loss is conveniently provided for subsequent evaluation. This is especially advantageous for orthodontia. Generally, the time in which interceptive orthodontia is initiated depends on the dates of loss of primary teeth. The dates provided on the tooth holder thus signal when orthodontia should begin.

The above is a brief description of some deficiencies in the prior art and advantages of the present invention. Other features, advantages and embodiments of the invention will be apparent to those skilled in the art from the following description, accompanying drawings and appended claims.

DESCRIPTION OF THE PREFERRED EMBODIMENT

Figure 1:
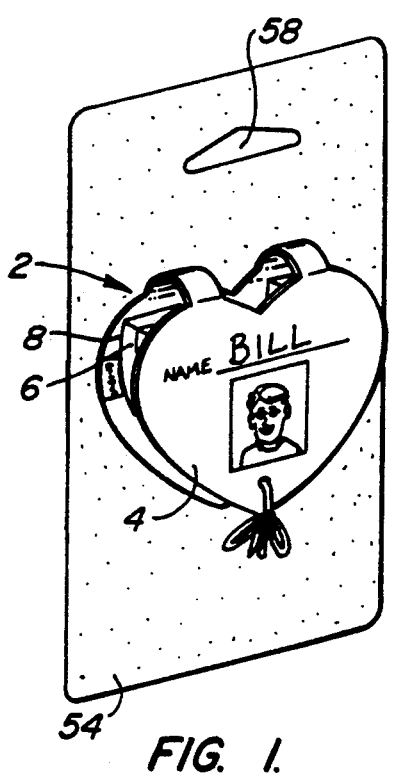
FIG. 1 is a perspective view of the tooth display holder secured to a display card in accordance with the principles of the present invention.

Referring to the drawings in detail, wherein like numerals indicate like elements, tooth holder 2 is shown in accordance with the principles of the present invention. Tooth holder 2 generally comprises casing 4 and generally U-shaped upper and lower tooth storage members 6, 8 which are essentially identical in construction.

Figure 3:
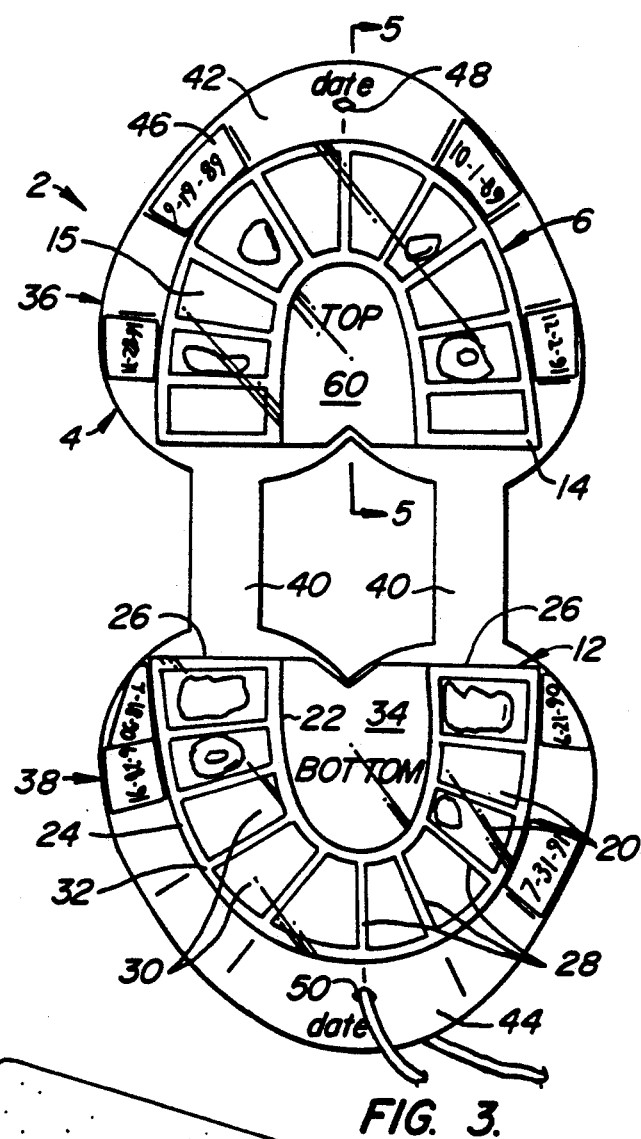
FIG. 3 is a top plan view of the display holder in the open condition.
Figure 4:
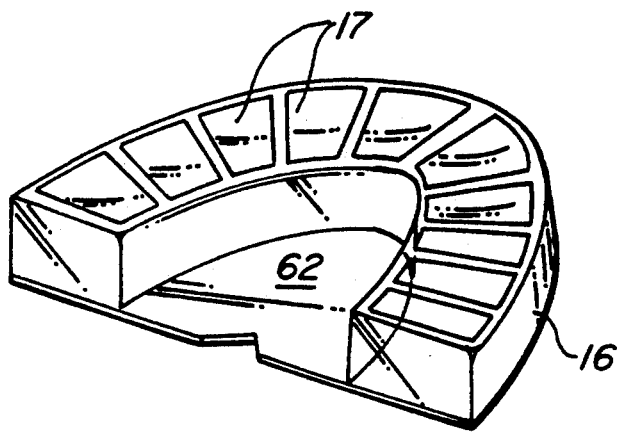
FIG. 4 is a perspective view of a detachable cover member for the tooth holder.
Figure 5:
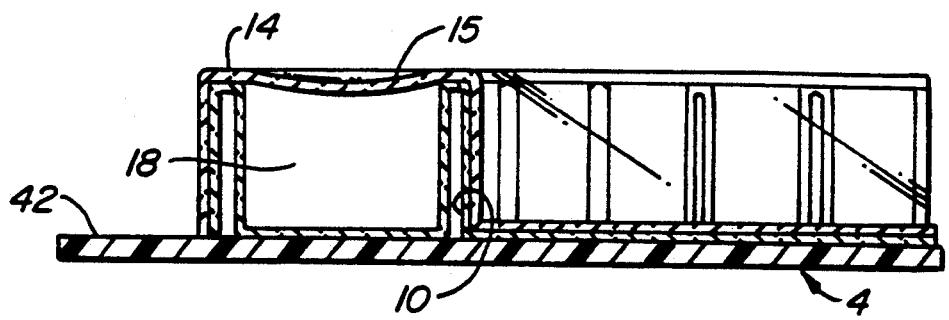
FIG. 5 is a sectional view of the tooth holder taken along line 5—5 in FIG. 3.

Referring to FIGS. 3-5, upper and lower storage members 6, 8 include essentially identical generally U-shaped upper and lower base members 10, 12 and essentially identical generally U-shaped cover members 14, 16. Each base member includes a plurality of receptacles or compartments 18, 20 that are sized to receive a particular tooth. Thus, although not shown to scale, the receptacles increase in size toward the end portions of each base member. Preferably, each base member includes 10 receptacles so that the tooth holder 2 can store a child's first 20 teeth. It is also preferred that each base member is formed as a single element, such as an integrally molded part, so that the receptacles are integrally connected and separation thereof is prevented. As illustrated in the drawings, each base and cover member is preferably a single piece of transparent plastic to facilitate viewing of the teeth that are placed in the tooth holder.

Figure 6:
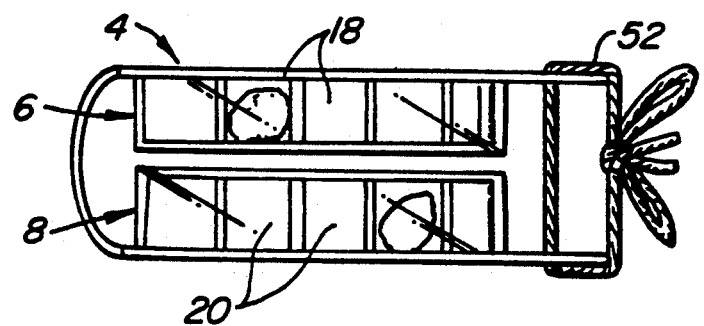
FIG. 6 is a side elevational view of the tooth holder in a closed position.

Since each base member is identically constructed, further description will be made with reference only to lower base member 12 for purposes of simplification Referring to FIGS. 3 and 6, base member 12 includes inner and outer U-shaped side walls 22 and 24, end walls 26, partition walls 28, and bottom walls 30. As evident from the drawings, walls 22, 24, 26, 28 and 30 form receptacles 20, each of which has an open end adjacent top surface 32 of base member 12. Base member 12 further includes web 34 which extends from the lowermost portions of inner wall 22 to form a substantially flat surface for securing the base member to casing 4, preferably by adhesive.

Referring to FIGS. 3 and 4, cover members 14, 16 are identical in configuration and have a shell-like configuration with a recess sized so that the cover members fit over upper and lower base members 10, 12 and form a friction fit therewith. In this way, the cover members are releasably attached to the base members. Each cover member further includes depressions 15, 17, along its upper surface. These depressions are configured to cooperate with and fit in the corresponding receptacles in the base members to enhance the securement between the cover and base members and further seal the open ends of the receptacles. The cover members further include webs 60, 62 (FIGS. 3, 4) each web being essentially identical to web 34. Specifically, webs 60, 62 are integrally formed with the cover members and enhance rigidity and, thus, reduce the tendency for the U-shaped sections to crack under torsion, for example.

Casing 4 includes upper and lower sections 36, 38 for supporting upper and lower storage members 6, 8, respectively. Sections 38 and 40 are pivotally connected to one another so that the tooth holder can be pivoted from an open position (FIG. 3) to a closed position (FIG. 6). As illustrated in FIG. 3, sections 36 and 38 are interconnected by arms 40 which form a hinge between the sections. This construction is especially advantageous for manufacture where the casing can thus be molded as a one-piece element or readily cut or stamped from a sheet or blank of flexible plastic having a thickness of about 116-1/8 inch, for example. The bottom portion of each base member is secured to the substantially flat inner surface of each casing support section 36, 38. Support sections are sized such that a portion of each support section extends radially outward from the respective base member to form shelves 42 and 44 for receiving a label 46 indicating the date of loss of a tooth placed in a receptacle adjacent the label. Alternatively, the casing can comprise or the shelf can include a layer of material suitable for print, such as paper or equivalents thereof, so that the date of loss can be marked directly on the tooth holder with no need for separate labels. Each shelf preferably has a width of about ¼ to ½ inch so that a label having sufficient size for easy viewing can be placed thereon without detracting from the compactness of the tooth holder for storage.

The casing also is provided with a fastening mechanism for holding the upper and lower casing sections together when the holder is placed in its closed position for storage. However, any suitable fastening mechanism can be used, as would be apparent to one of ordinary skill, for example, a mechanism that extends between the upper and lower sections of the casing and is provided with complementary snap fasteners. As illustrated in the drawings, such a mechanism can be provided by placing holes 48, 50 in the upper and lower sections 36, 38 for receiving string 52 which can then be tied to retain the holder closed as illustrated in FIG. 6. It is further preferred that the casing be opaque to provide a background for observing the teeth through transparent storage members 6 and 8 and to reduce the amount of sunlight that can reach the teeth placed in the receptacles to prevent discoloration thereof, for example.

As discussed above, the tooth holder is especially suited for storage and display of young children's first teeth after the teeth fall. That is, as young children's first teeth become detached from their natural support structure, i.e., the maxilla, mandible, gums and surrounding tissue, they are placed in a corresponding receptacle in one of the base members, both of which are configured to simulate the upper and lower supporting arches of a person's mouth. A self-adhering label is then filled out to identify the date of tooth loss and the label affixed to a portion of the casing shelf adjacent the receptacle in which the tooth is placed. When the shelf comprises a material suitable for receiving print (e.g., when the casing is formed from a heavy weight paper product), the date is directly marked on the appropriate portion of the shelf. Although the tooth holder has been described for use in storing a child's first twenty teeth, an embodiment in which the upper and lower base members each include ten receptacles, the tooth holder can be provided with a greater number of receptacles if it is desired to keep a record of the loss of adult teeth.

Figure 2:
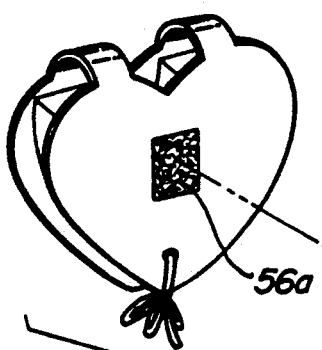
FIG. 2 is an exploded view of the assembly illustrated in FIG. 1 showing the fastener for securing the holder to the display card.

Referring to FIGS. 1 and 2, the tooth holder also can be constructed to include a display card 54 removably secured to the back of the lower base member 12, such as by complementary strips of hook and loop fastening material 56a, b (FIG. 2). Display card 54 includes aperture 58 configured to received a conventional hanger so that the tooth holder can be hung and, thus, displayed when in the closed position. In this way, the outer surface of the upper casting section provided with the person's identification, such as the person's name and photograph (FIG. 1), can be readily displayed.

The above is a detailed description of a particular embodiment of the invention. It is recognized that departures from the disclosed embodiment may be made within the scope of the invention and that obvious modifications will occur to a person skilled in the art. The full scope of the invention is set out in the claims that follow and their equivalents. Accordingly, the claims and specification should not be construed to unduly narrow the full scope of protection to which the invention is entitled.

What is claimed is:

1. A tooth holder comprising:
   a casing including first and second support members and a hinge that pivotally couples said support member to one another, each support member having an outer surface and a substantially flat inner surface;
   first and second generally U-shape storage members, each storage member including a generally U-shaped base member and a cover member, each base member having a plurality of receptacles formed therein and each cover member having a recess configured to receive one of said base members, each base member having a bottom portion secured to the inner surface of one of said support members and arranged such that a portion of each support member extends radially outward beyond a respective base member, said radially extending portions each forming a shelf for receiving indicia thereon.

2. The holder of claim 1 wherein each recess has a configuration such that when one of said cover members is positioned over one of said base members a friction fit is formed therebetween.

3. The holder of claim 1 wherein said shelf comprises paper.

4. The holder of claim 1 wherein said casing is integrally formed as a one-piece element.

5. The holder of claim 4 wherein said first and second support members are displaceable between an open position in which said support members and hinge are substantially in the same plane and a closed position in which the storage members are positioned one on top of the other.

6. The holder of claim 5 including means for retaining the holder in said closed position.

7. The holder of claim 1 wherein each shelf extends radially beyond a respective storage member at least about ¼ inch.

8. The holder of claim 7 wherein said shelf extends radially beyond a respective storage member about ¼ to ½ inch.

9. The holder of claim 1 wherein each base is an integrally formed one-piece element.

10. The holder of claim 1 wherein said base and cover members are transparent.

11. The holder of claim 10 wherein said casing is opaque.

12. The holder of claim 1 wherein each base member includes ten receptacles.

13. The holder of claim 1 further including a display card and means for securing the holder to said display card.

14. A tooth holder comprising:
a casing including first and second support members and a hinge that pivotally couples said support members to one another, each support member having an outer surface and a substantially flat inner surface;
first and second generally U-shaped base members each being an integrally formed one-piece element and having a plurality of receptacles formed therein and configured for receiving a person's tooth, each base member being secured to the inner surface of one of said support members and being oriented such that a portion of each support member extends radially outward beyond a respective base member forming a shelf having a width of at least about ¼ inch; and
first and second cover members, each cover member having a configuration that generally corresponds to that of one of said base members.

* * * * *